United States Patent [19]
Bohl et al.

[11] 3,975,160
[45] Aug. 17, 1976

[54] COLORIMETRIC ANALYZER

[75] Inventors: Thomas L. Bohl, Clearwater; Lyman E. Goodnight, Jr., St. Petersburg; Herschel C. Ruble, Clearwater; John H. Wells, Seminole, all of Fla.

[73] Assignee: Milton Roy Company, St. Petersburg, Fla.

[22] Filed: July 29, 1974

[21] Appl. No.: 492,725

[52] U.S. Cl. .............................. 23/253 R; 250/564
[51] Int. Cl.² ........................................ G01N 21/24
[58] Field of Search ............ 23/253 R, 259; 356/180, 356/181; 250/564, 565, 576

[56] References Cited
UNITED STATES PATENTS

| | | | |
|---|---|---|---|
| 3,028,225 | 4/1962 | Sheen | 23/253 R |
| 3,030,192 | 4/1962 | Schneider, Jr. | 23/253 R |
| 3,476,516 | 11/1969 | Curry | 23/254 R |

OTHER PUBLICATIONS

Fisher Scientific Co., Modern Laboratory Appliances, 1942, p. 65.

*Primary Examiner*—Robert M. Reese
*Attorney, Agent, or Firm*—Woodcock Washburn Kurtz & Mackiewicz

[57] ABSTRACT

A colorimetric analyzer automatically and continuously measures the transmission of light through a sample which has been mixed with reagents. Precise volumes of the sample are repeatedly measured by a siphon tube. Volumes of the reagent are added to the sample at different times in a measuring cycle. The reagent is added at different places in the analyzer so that it is possible for two different time-consuming reactions to proceed simultaneously. The mixed reagent and sample is supplied to a measuring cell which includes a source of light and a photocell. The distance between the source of light and the photocell are adjustable to accommodate analyses of mixtures with widely varying light transmission while providing a full scale output indication. The output of a photocell is applied to a sample and hold circuit during time intervals when the reactions of the reagents with the sample have been completed.

17 Claims, 14 Drawing Figures

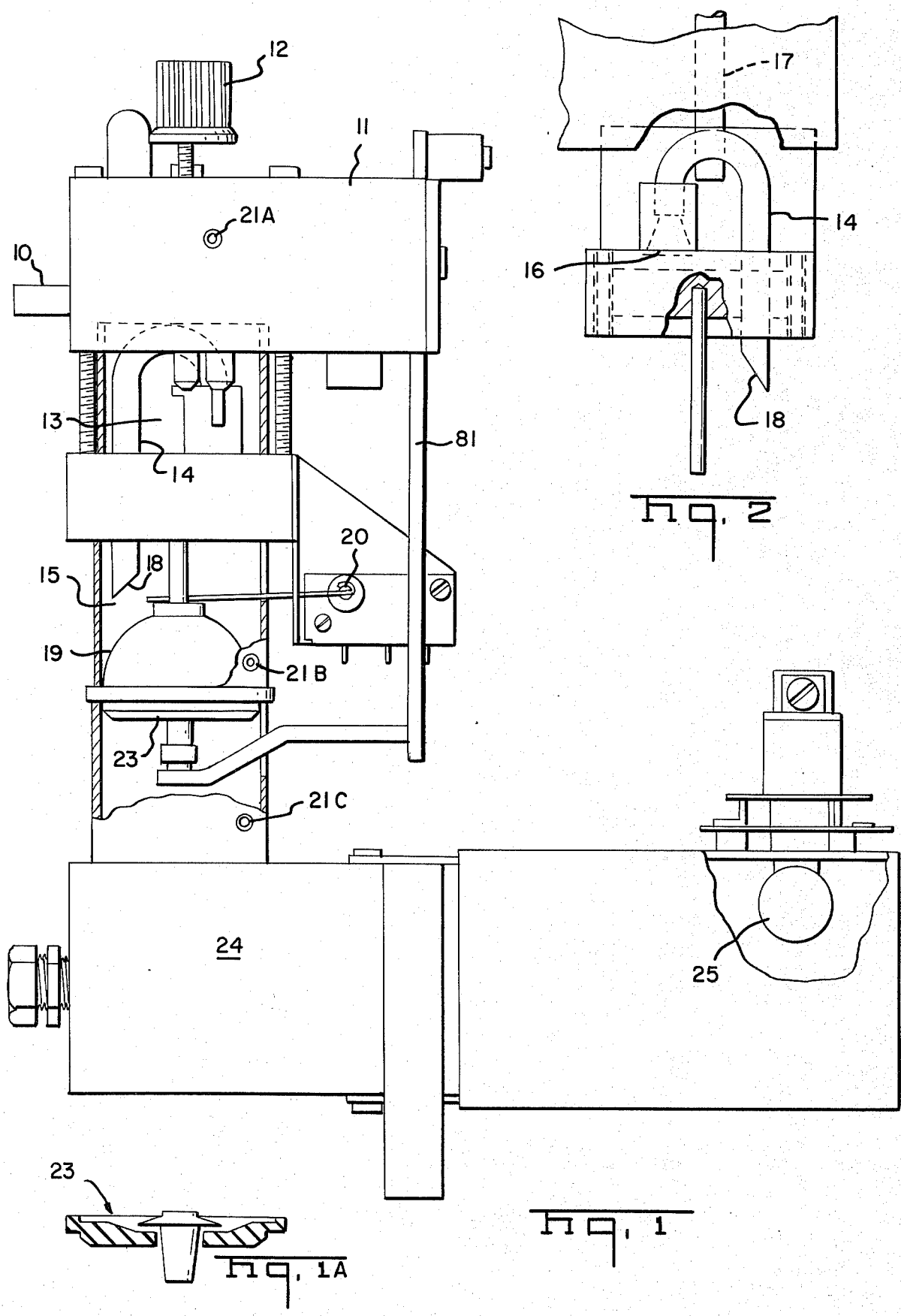

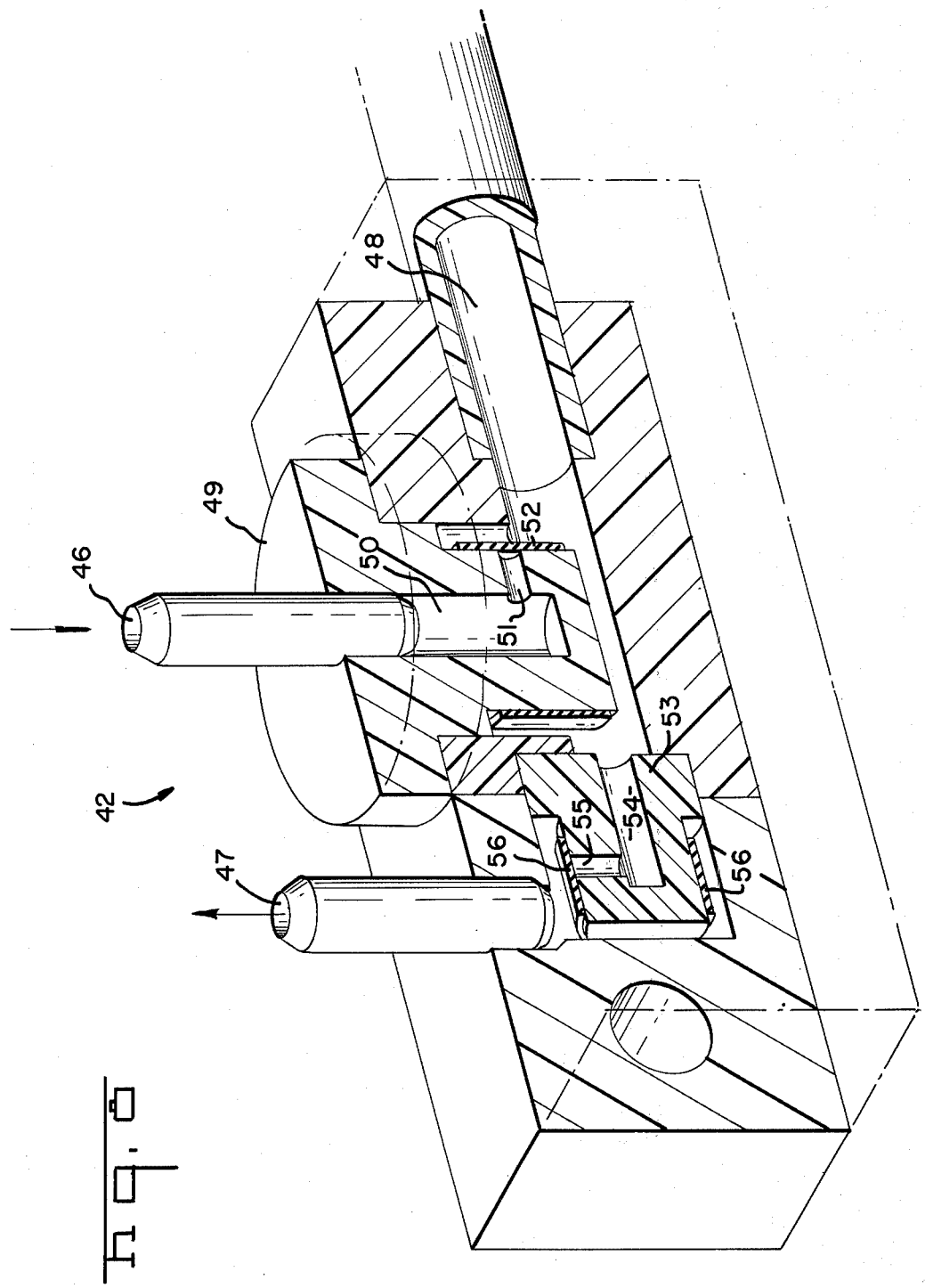

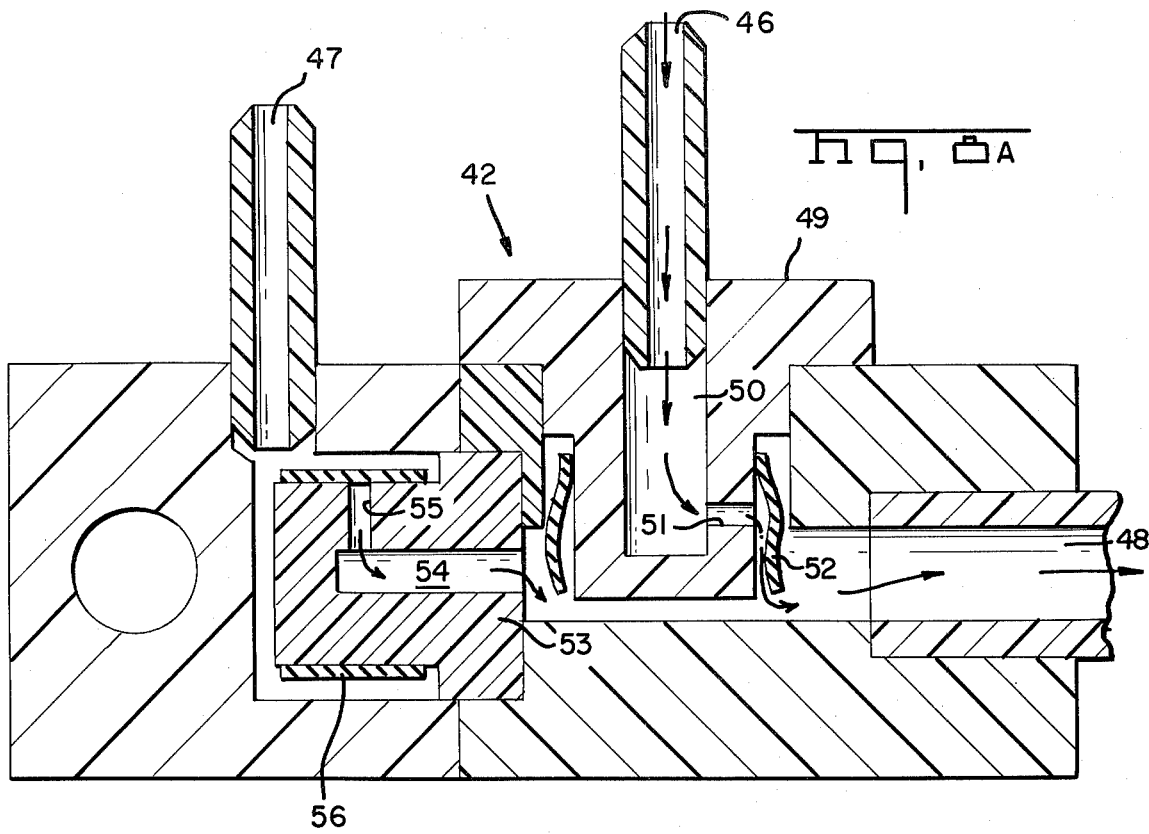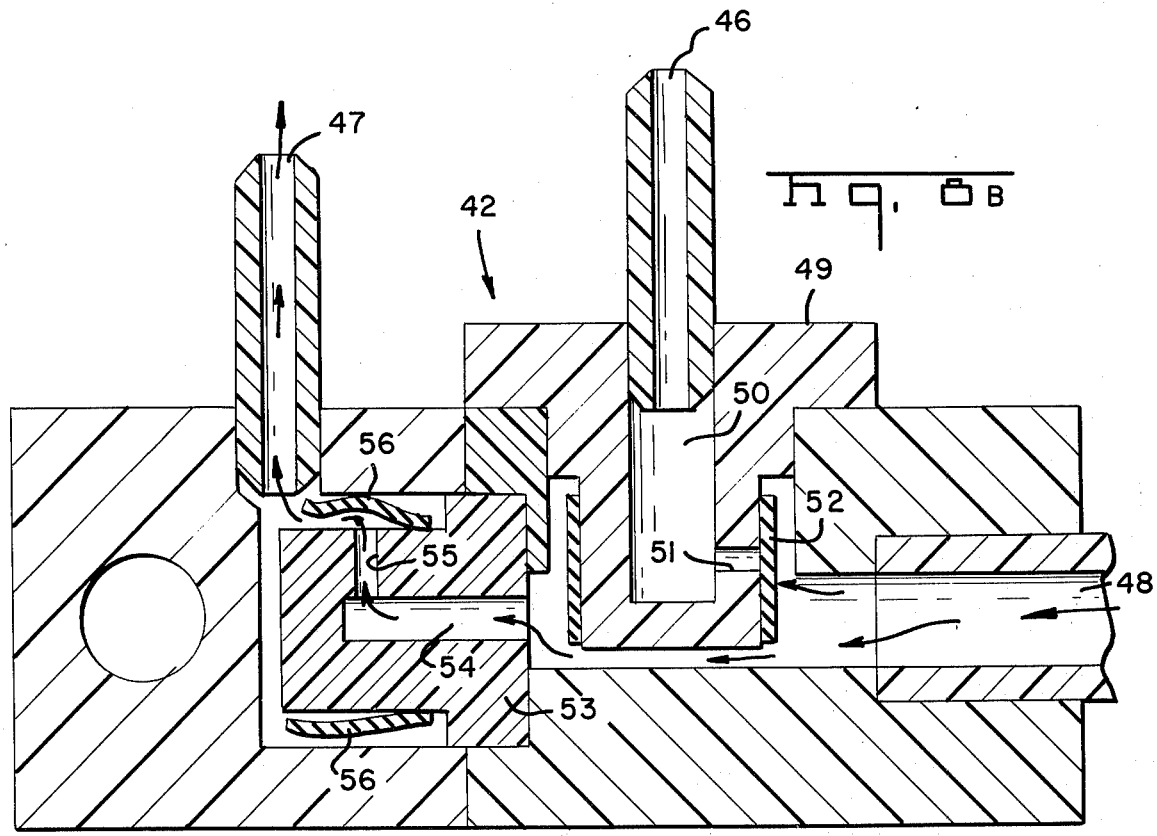

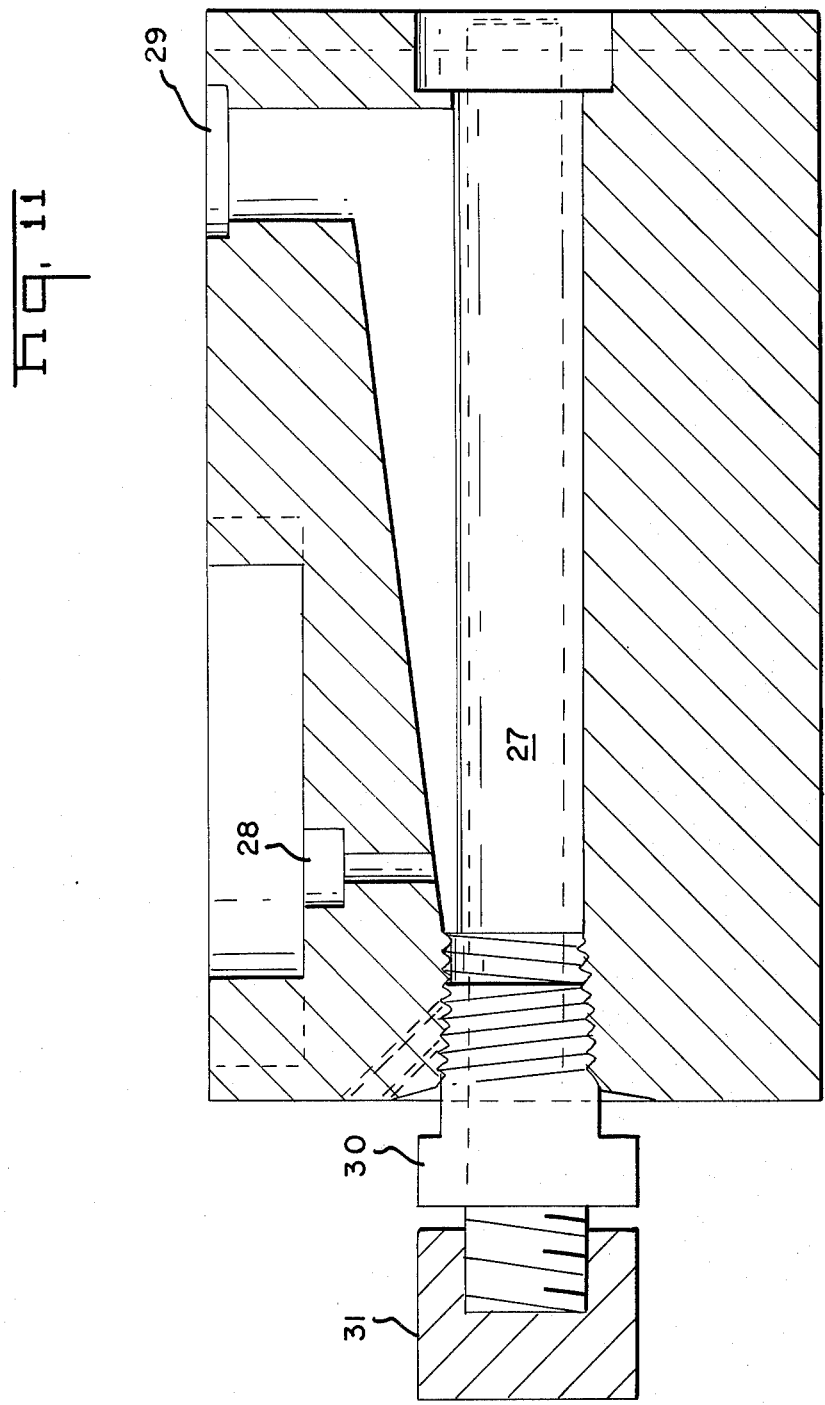

COLORIMETRIC ANALYZER

BACKGROUND OF THE INVENTION

This invention relates to colorimetric analyzers, and more particularly to an analyzer for automatically and sequentially delivering a plurality of reagents and providing for time delays to allow reactions of the reagents with the sample to go to completion.

Colorimetric analyzers are extensively used in laboratory and industrial work to determine the constituents of a sample mixture. For example, colorimetric analysis is used to determine water hardness, to test for orthophosphate content and to test for silica in a sample.

U.S. Pat. No. 3,028,225, issued Apr. 3, 1962 to Robert T. Sheen describes a colorimetric analyzer in which the light source is divided into two beams, one of which passes through a test sample to a first photocell, and the other of which falls on a second photocell. The Sheen system includes two stopcocks which are continuously driven by a motor. These two stopcocks respectively deliver reagent and sample to a precise volume chamber. At periodic times, the precise volume is delivered to a sample cell where a continuous measurement of light transmitted through the sample is made.

Automatic chemical analyzers of this type are important because they do not require the constant attention of a technician to obtain accurate measurements. Improvement on this type of apparatus is needed in respect to providing flexibility of adding more than one reagent and in respect to allowing the reactions to go to completion before measurements are made.

SUMMARY OF THE INVENTION

In accordance with this invention, a colorimetric analyzer automatically measures light transmission through a reacted sample only during time intervals when the reactions of reagents with the sample have been completed. The colorimetric analyzer provides the flexibility for adding up to three reagents to the sample automatically and providing time delays for each of these reagents to react completely with the sample before a measurement is made. This flexibility allows the analyzer to be used for colorimetric analysis of water hardness, orthophosphate content, testing for silica and other tests for which it is desireable to use a colorimetric analyzer.

In accordance with an important aspect of this invention, a siphon tube provides the means for metering precise amounts of sample. The siphon tube has an entry end which is larger in diameter than the remainder of the tube to spread the surface tension of the sample over a larger area whereby the meniscus of the sample in the entry end breaks at a repeatable point. The dispensing end of the siphon tube is biased to prevent drops of sample from hanging to the end of the siphon, thereby blocking the end of the siphon.

In accordance with another important aspect of this invention, the distance between the light source and the photocells is adjustable to accommodate analyses of samples having different light transmissions with full scale range of the indicator.

In accordance with another aspect of the invention, the reagent dispensing means includes a spool valve which delivers precise volumes of reagent.

In accordance with another aspect of this invention, the system is fail-safe if a stoppage in the flow of sample occurs. If this happens, reagent will not be delivered by the system. Also, in the event of an electrical failure, reagent and sample will not be delivered by the system.

The foregoing and other objects, features and advantages of the invention will be better understood from the following more detailed description and appended claims.

DESCRIPTION OF THE DRAWINGS

FIG. 1 is a side view of the colorimeter showing the metering and float chambers in section;

FIG. 1a is a cross-sectional view of a valve assembly used in the colorimeter.

FIG. 2 shows the siphon tube in more detail;

FIG. 3 is a side view of the analyzer showing the syringes and the tube supplying reagents to the different chambers in the measuring column;

FIG. 8 shows the spool valve for the reagent dispensing;

FIGS. 8A and 8B show the spool valve operation;

FIG. 11 is a side sectional view of the measuring cell on the lines 11—11 of FIG. 10.

DESCRIPTION OF THE PREFERRED EMBODIMENT

Figure 7:
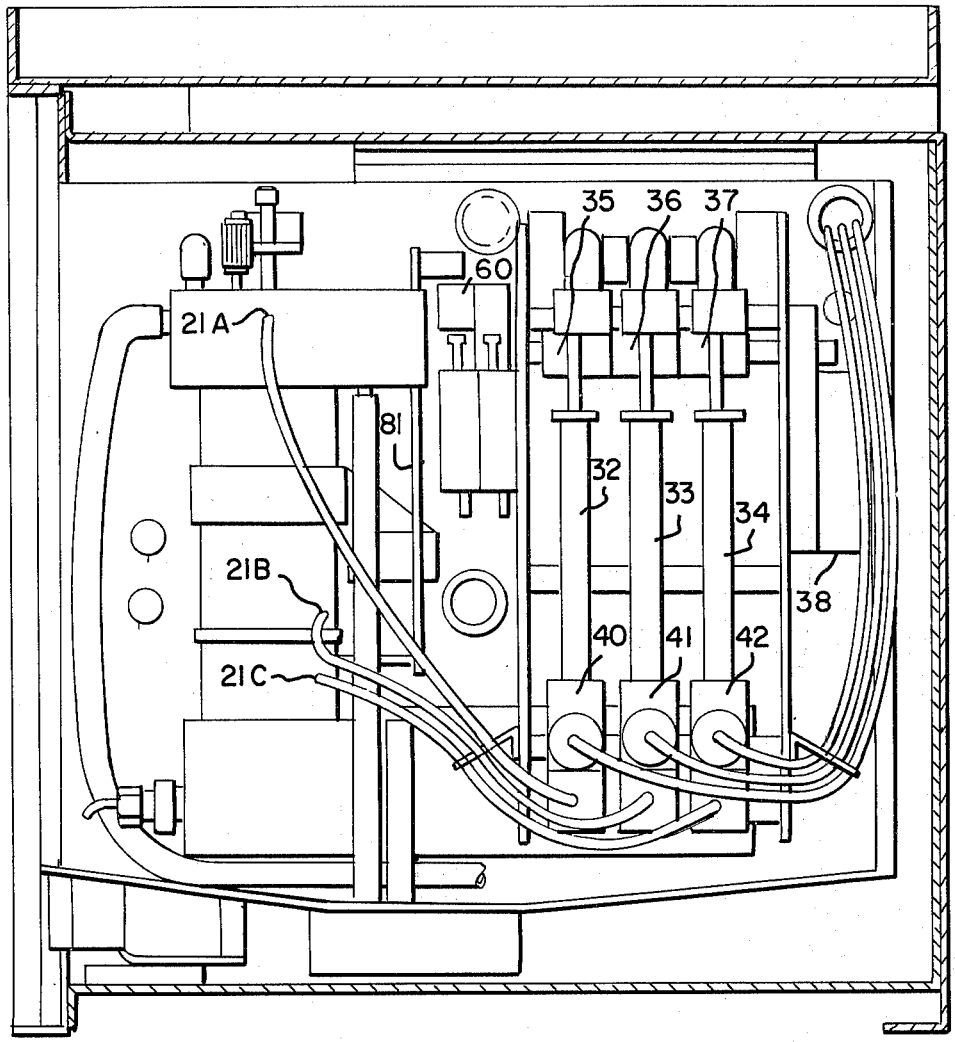
FIG. 7 is a front view of the cam assembly of FIG. 5.
Figure 4:
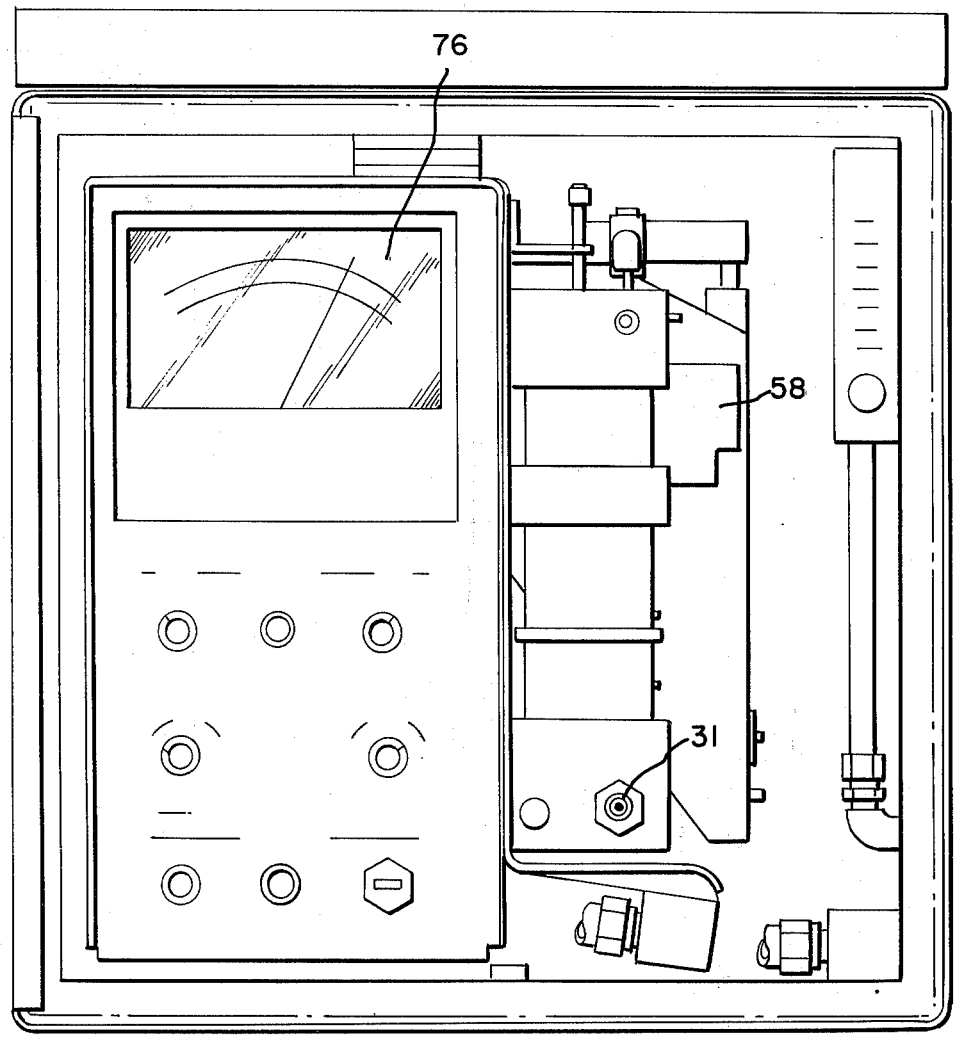
FIG. 4 is a front view showing the meter.

The sample to be analyzed is supplied to inlet 10 of sample block 11. A needle valve in sample block 11 is adjustable by the knob 12 to provide a drop-by-drop flow of sample into the metering chamber 13. The placement of the needle valve in the bottom wall of the passageway through sample block 11 is important. In this position the valve is immune to gas bubbles in the sample stream so the valve will not air bind at the required low flow rate. As an example, a 20 milliliter aliquot of sample is delivered drop-by-drop to the metering chamber 13 over the time period of the analysis cycle. The adjustable needle valve times the number of drops per minute and hence determines the length of the measuring cycle. One drop per second results in a measuring cycle of approximately three minutes in the example. Analysis accuracy is completely immune to main sample flow rate.

The drop-by-drop sample is collected in the metering chamber 13 which is directly beneath sampling block 11 by way of a vent tube 17 which extends through the top of chamber 13. A siphon tube 14 in the metering chamber delivers a precise volume of fluid to the float chamber 15. The siphon tube has an entry end 16 (FIG. 2), an apex and a dispensing end 18. A vent tube 17 extends through the sample block 11 to about the level of the entry end 16. The chamber 13 is completely sealed except for the vent tube 17 and the siphon tube 14 which extends through the bottom of chamber 13. The chamber 13 fills drop-by-drop until the bottom of the vent tube 17 is closed by the sample. At this point, the level of sample does not rise further in the chamber 13, but it does rise in the vent tube 17 and in the siphon tube 14. A siphon action is started which delivers a precise amount of fluid through the dispensing end 18 of the siphon to the float chamber 15. The vent tube 17 provides the means by which the siphoning action precisely is started. After the end of vent tube 17 is covered, siphoning action is started within a few drops which is all that is required to fill the siphon tube. Note that without the provision of vent tube 17, many drops would be required to fill the chamber 13 up to the apex of the siphon tube. The amount required could vary from operation to operation. However, the positioning of the siphon tube 14 and vent tube 17 as shown deliver precisely repeatable volumes of sample.

Other features which contribute to this accuracy are shown in FIG. 2. The entry end 16 of the siphon tube is larger in diameter than the remainder of the tube. Because of this, the surface tension of the sample is spread over a larger area. Because of this, the meniscus of the sample in the entry end breaks at a repeatable point each time a siphoning action is performed. While the siphon tube is shown with a funnel shaped entry end in FIG. 2, a bell shaped entry end may also be used. Other shapes are possible for use. The siphon tube 14 must be of small enough diameter to produce a good siphon action, but we have found that a larger diameter on the entry end of the siphon tube contributes greatly to metering accuracy. Also, the dispensing end 18 of the siphon tube is cut at a bias. This bias prevents drops of sample from hanging to the end of the siphon tube. Such drops would otherwise possibly block the end of the siphon tube and prevent accurate siphoning action.

Referring back to FIG. 1, the float chamber 15 houses a float 19 which actuates a switch 20 which starts the timer motor. The timer motor actuates syringes which deliver volumes of reagent to the analytical column. When the supply of sample is interrupted for some reason, the timer motor is not started so the analyzer is not swamped with reagent during a time when no sample is available.

Reagent ports 21A, 21B and 21C are provided to supply different reagents to the analytical column. In the example being described, the sample is held in float chamber 15 for one minute and reagent may be injected into the sample during this time. At the end of 1 minute, the timer motor opens a valve 23 which includes a silicone rubber plug (FIG. 1A). This allows the reacted sample to flow from the float chamber 15 into the measuring cell 24. Light from a lamp 25 is transmitted through the reacted sample in the measuring cell 24 to two photocells which are positioned in the measuring cell.

Figure 10:
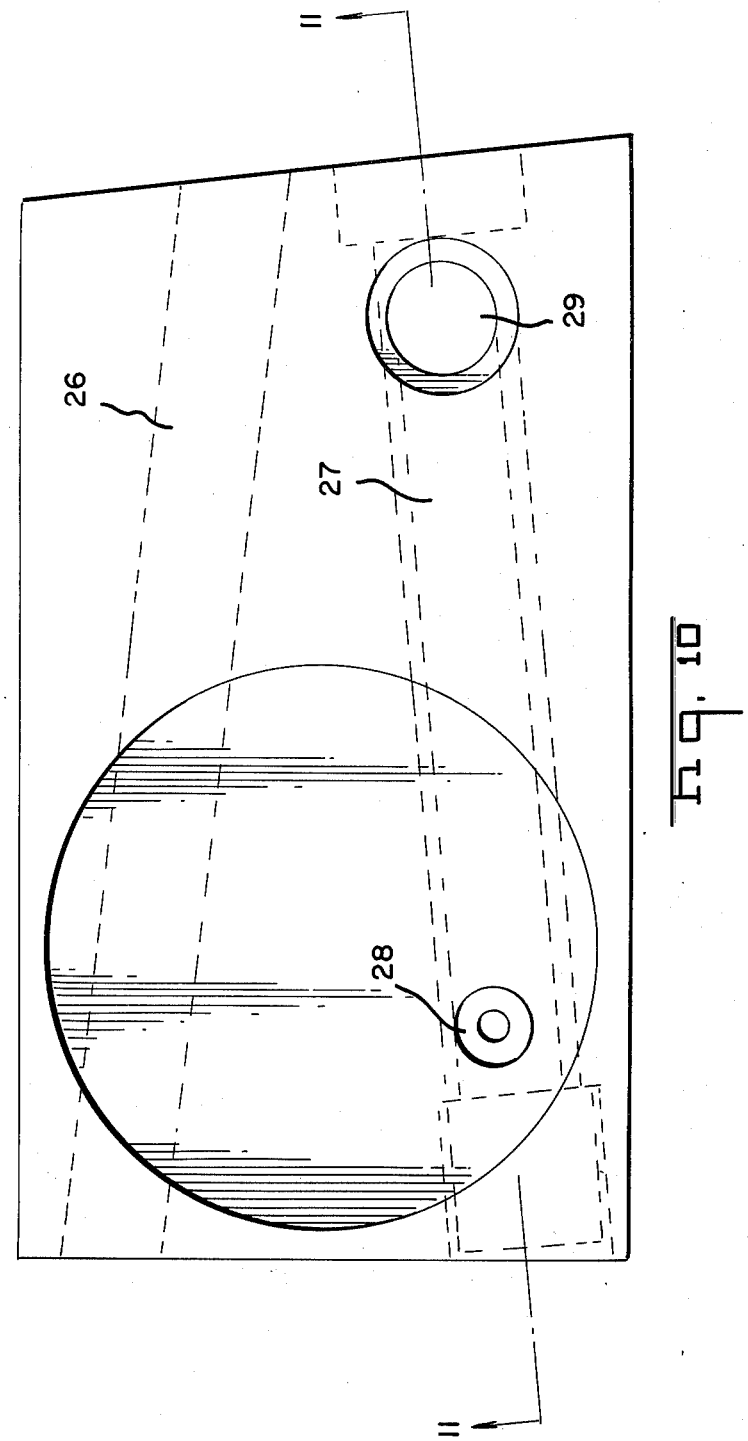
FIG. 10 is a top view of the measuring cell.

The measuring cell is shown in more detail in FIGS. 10 and 11 which respectively show a top view and a side sectional view of the measuring cell. A reference photocell is positioned in the chamber 26 and a measuring photocell in the chamber 27, (For purposes of clarity, the photocells are not shown in FIGS. 10 and 11).

Reacted sample enters the measuring cell through the port 28. The chamber 27 holds about one third of the total volume dumped into the measuring cell from the float chamber. The remainder overflows through the overflow outlet 29. The overflow outlet is upcut to prevent bubbles from accumulating in the chamber 27. The distance between the measuring photocell in chamber 27 and the light source 25 is adjustable. The measuring photocell assembly 30 is adjustably threaded into the measuring cell. A swage fitting 31 locks the photocell into the selected position. This provides the means for adjusting the relative position between the light source 25 and the photocell to accommodate analyses of samples having different light transmissions with full scale range of the indicator.

FIG. 3 shows the reagent dispensing means. Syringes 32, 33 and 34 deliver precise volumes of reagent to the reagent ports 21A, 21B and 21C in the metering chamber, float chamber and measuring cell respectively. The operator has the option of connecting some or all of these syringes to supply reagent to the analytical column. For example, in the analysis for silica, it is necessary to deliver precise amounts of three reagents to be reacted with the sample. In such a situation, all three syringes 32–34 are used but in other analyses not all are required.

In the case of a silica analysis, two time consuming chemical reactions can be progressing simultaneously, one in the metering chamber and one in the measuring cell. This overlap can provide a five minute measuring cycle, faster than any present commercially available silica analyzer. This is an important feature of this invention. It is important that cycle time is limited only by the time required for the chemical reactions to go to completion. In the case of water hardness analysis, the reaction is essentially instantaneous. In that case, cycles could be repeated after each timing motor revolution. In practice, a 2-minute-per-revolution timing motor and a five minute sample cycle have been provided to conserve reagents. One-minute-per-revolution motors have been successfully used.

Figure 5:
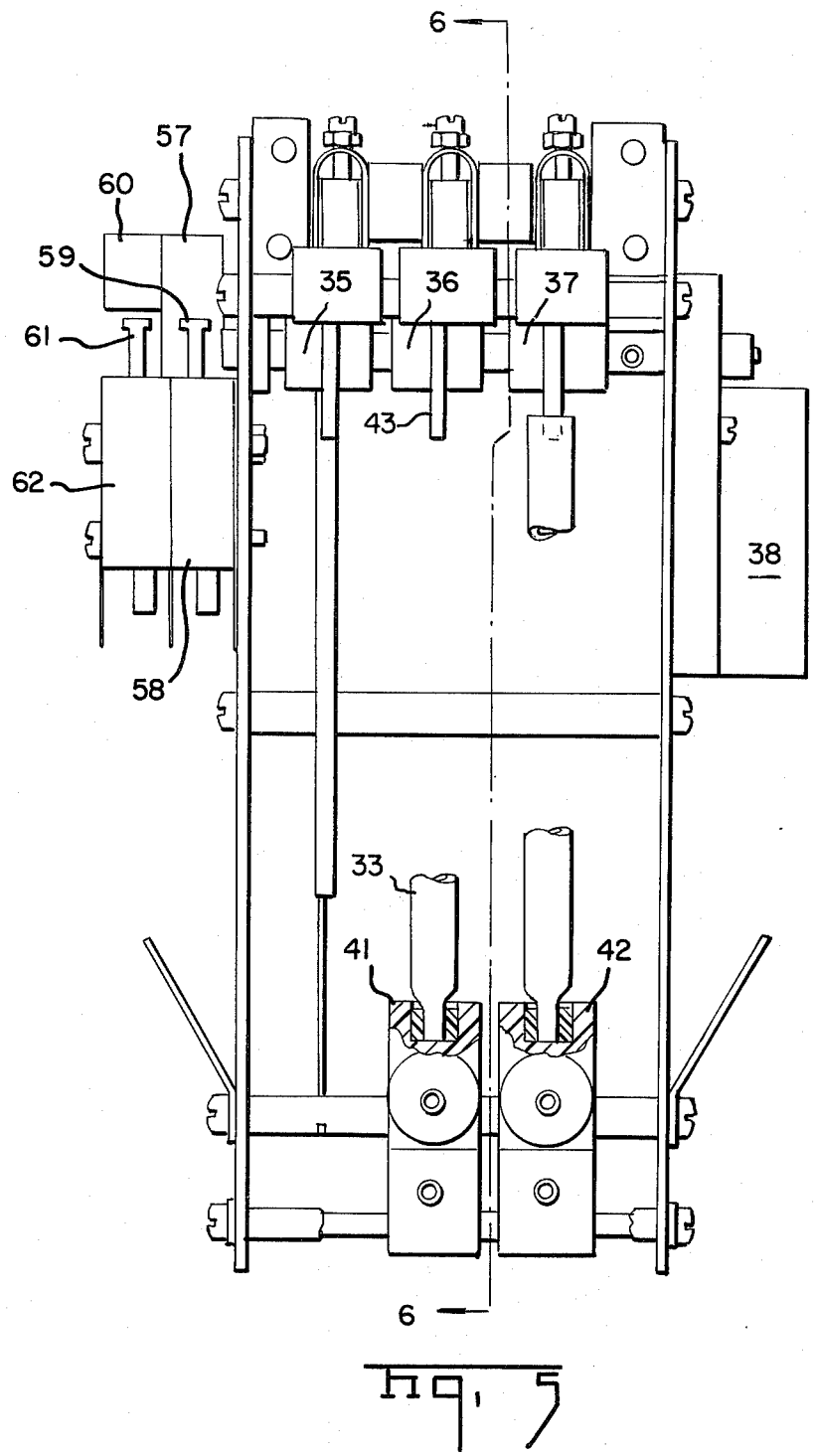
FIG. 5 shows the cam assembly.
Figure 6:
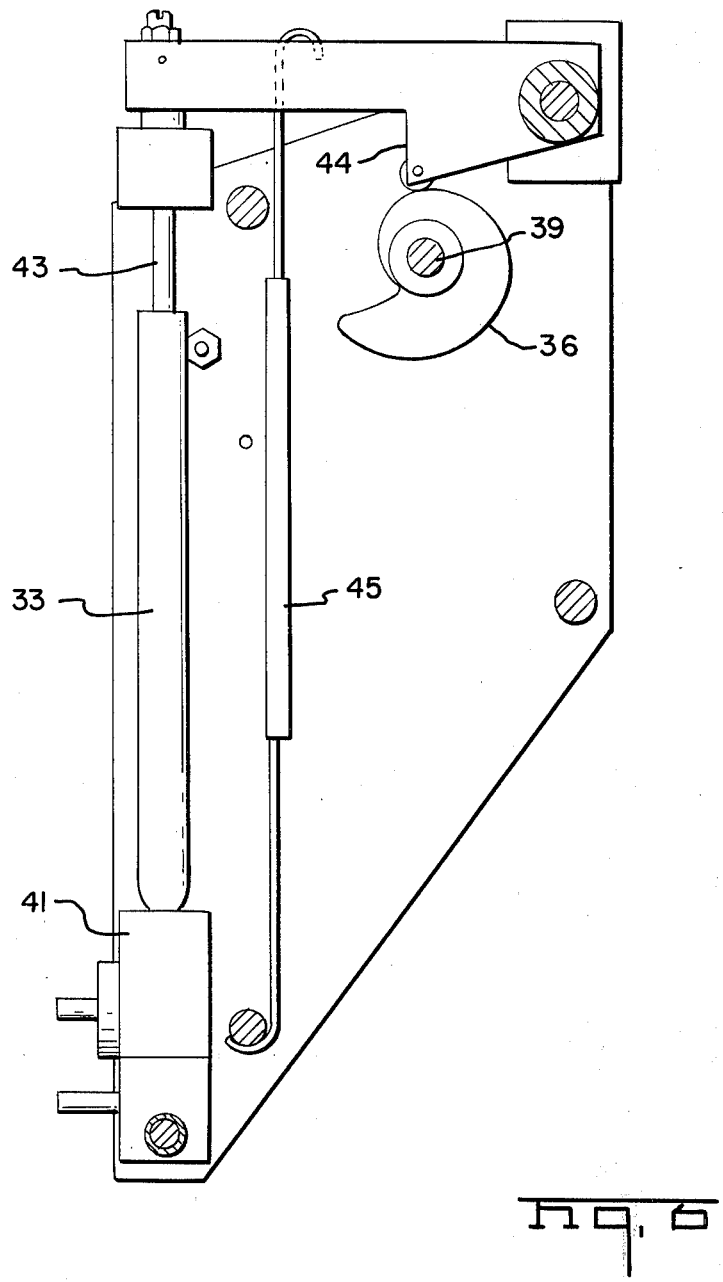
FIG. 6 is a section through the line 6—6 of FIG. 5.
Figure 7:
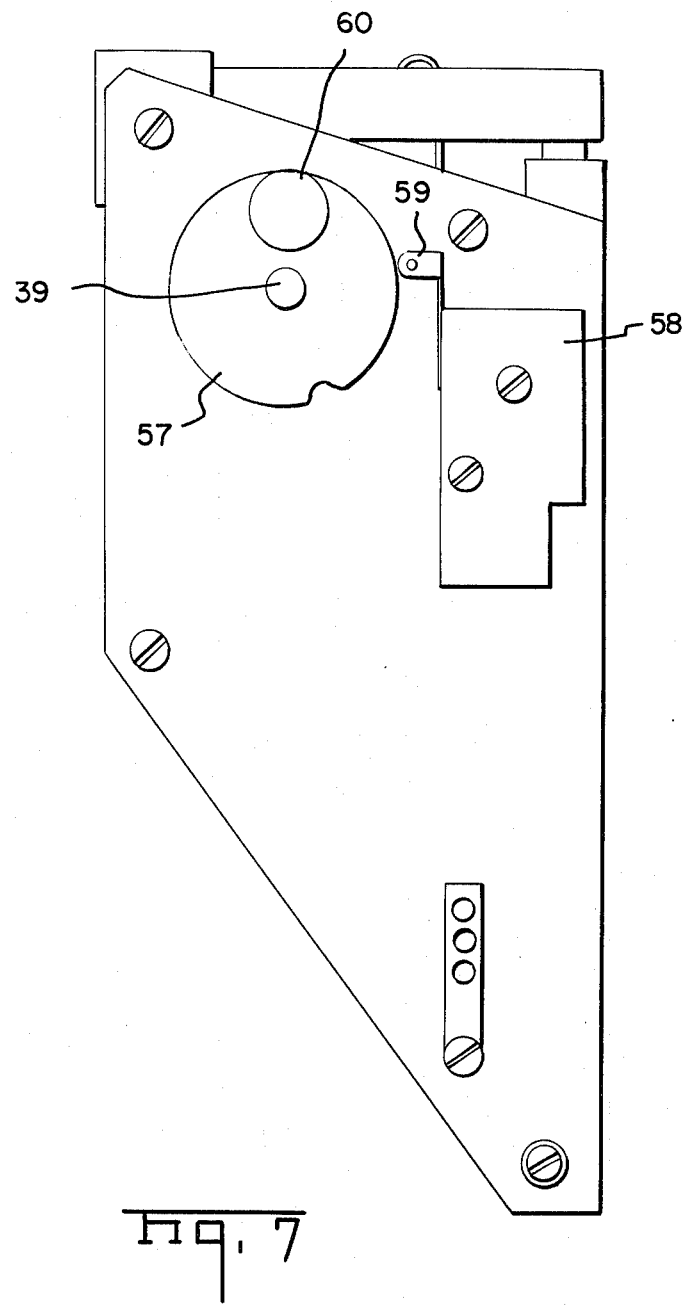

Each syringe includes a plunger 43 (FIGS. 5 and 6) which is raised to fill the syringe and which is lowered to dispense reagent to the analytical column. The syringe plungers are driven by cams 35–37. The cams are, in turn, rotated by the timing motor 38. All of the cams are mounted on a common shaft 39 (FIG 6). The cam driven syringes 32–34 deliver reagents to the sample at appropriate times in the analysis cycle, which times are determined by the cams 35–37. The cams have a spiral profile as seen in FIG. 6 so that the syringes are slowly filled and then are rapidly discharged by spring force. The rapid discharge of reagents into the sample promotes good mixing. The plunger 43 is operated by the cam follower 44 which is biased downwardly by the spring 45.

Small sleeve and spool valves 40, 41 and 42 are provided on the inlet and outlet of each syringe. Since the analyzer accuracy is directly dependent on the accuracy of the reagent volume delivered, positive acting check valves are required. These valves are an important aspect of this invention and they are shown in FIG. 8. Each valve includes an inlet 46 which is connected to a supply of reagent. Outlet 47 is connected to one of the reagent ports 21A, 21B or 21C in the analytical column. The opening 48 is connected to the syringe. The spool-like element 49 has an axial inlet 50 and a radial discharge port 51. An elastomer sleeve 52 is positioned around the circumference of the spool 49.

As shown in FIG. 8A, pressure applied to the inlet 46 of the valve forces fluid through axial inlet 50, through radial discharge port 51, past the elastomer sleeve 52 and through the opening 48 to the syringe. FIG. 8B depicts the syringe being discharged. The pressure holds the elastomer sleeve 52 tightly against the port 51 to prevent any of the precisely measured volume of reagent from escaping through the port 51.

The valve between the syringe and the reagent port on the analytical column is similar. It includes a spool-like element 53 having an axial inlet 54 and a radial discharge port 55. An elastomer sleeve 56 tightly covers the discharge port 55. When the syringe is being discharged, pressure of the fluid forces the fluid through the axial inlet 54, out of the radial discharge port 55, past the elastomer sleeve 56 and out of the outlet 47 to one of the reagent ports 21A, 21B or 21C. When the syringe is being filled, the suction exerted by the syringe plunger on the opening 48 pulls the sleeve 56 into tight sealing relationship with the port 55. This prevents any of the precise volume previously delivered to the analytical column from being drawn back into the syringe.

FIG. 7 shows the measuring cam 57 which actuates the measurement switch 58. At the appropriate time in the measuring cycle, the follower 59 moves into an indentation in the measuring cam 57. This operates measurement switch 58. As best seen in FIG. 5, the cam 57 has a cam nose 60 which operates the lever 61 on the run switch 62. The function of the run switch is to keep the timer motor energized after an analysis cycle has been initiated by closure of the float actuated switch.

Figure 9:
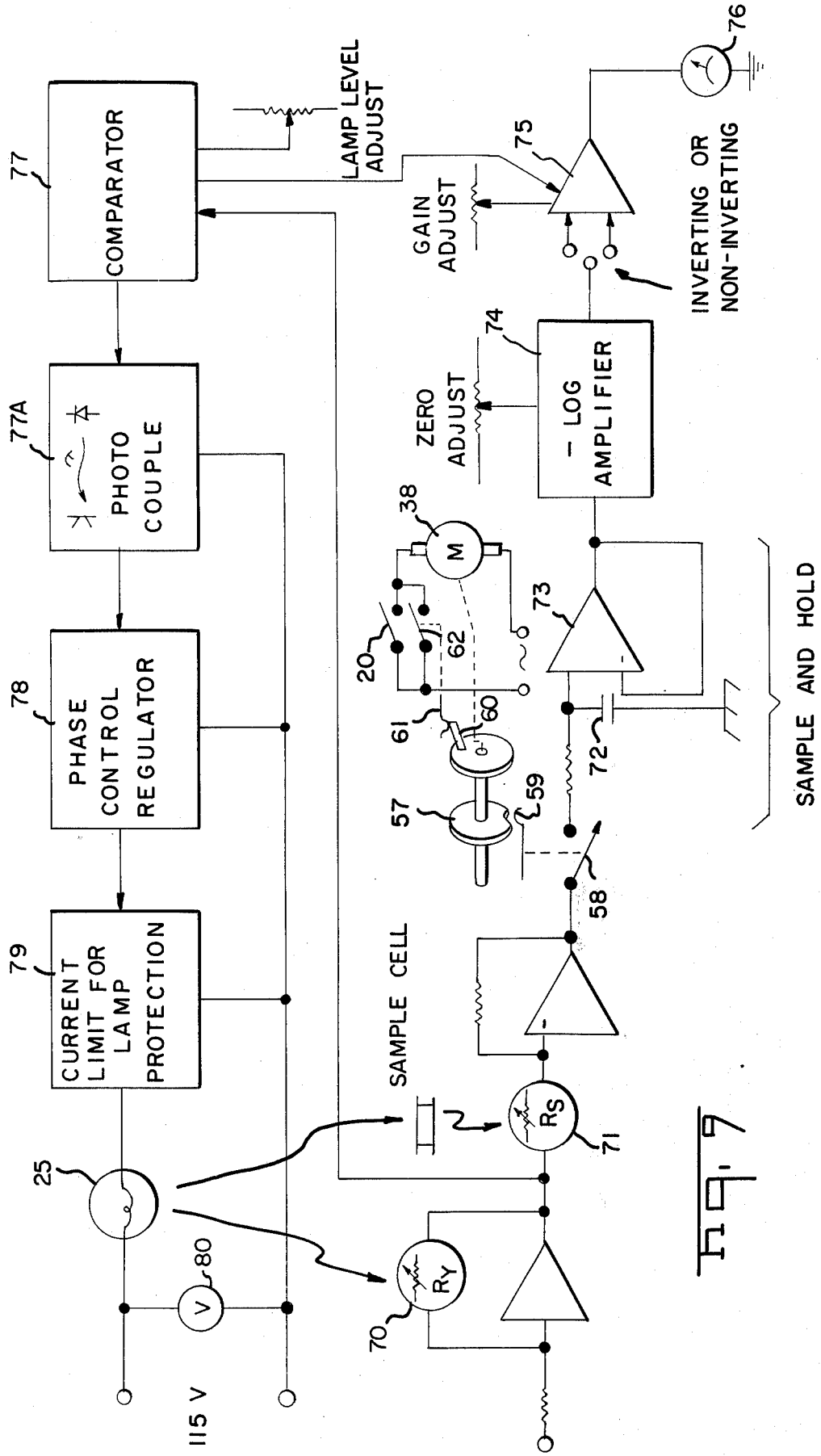
FIG. 9 is a block diagram of the electrical system.

Referring to the electrical block diagram of FIG. 9, the reference photocell 70 and the measuring photocell 71 form part of an amplifier bridge circuit in which the ratio of the light intensity reaching each cell is translated into a voltage. This voltage is sampled during each analysis cycle by closure of the measurement switch 58. As previously discussed, the cam 57 driven by the timing motor 38 closes the measurement switch 58 for approximately five seconds during each analysis cycle. The voltage is applied to a sample and hold circuit which includes capacitor 72 and operational amplifier 73. A logarithmic amplifier 74 converts the logarithmic signal from the photocells to a linear signal suitable for displaying on linear meter scales and for driving conventional analog recorders, controllers and other devices. Amplifier 75 provides means for adjusting the electronic zero. The output of amplifier 75 is applied to the meter 76 and it is applied to an output which may be connected to a recorder or other suitable indicator.

The control circuitry for the lamp 25 regulates the lamp to maintain a constant brightness. The reference photocell 70 obtains light from the lamp which has passed through light filters. The output of reference photocell 70 provides a feedback signal which is applied to the comparator 77. This compares the output of reference photocell 70 with a level adjust signal. The output of comparator 77 is applied to a photocouple 77A which includes a light emitting diode and a light sensitive transistor. This converts the output of the comparator into a signal which changes the duty cycle of an SCR driver in the regulator 78. This controls the brightness of the lamp 25. The usual current limiting circuit 79 is provided.

A solenoid valve 80 is connected across the line voltage. In the case of a power failure, valve 80 cuts off flow of sample to the analyzer.

The operation of the colorimetric analyzer will be described with regard to a particular example. Assume that the knob 12 on the needle valve is adjusted to produce approximately 36 drops per minute of sample into the metering chamber 13. After about five minutes, the level in the metering chamber reaches the apex of the siphon tube. The siphoning action starts and siphons a precise amount of sample into the float chamber 15. The float 19 rises and closes the float actuated switch 20. This energizes the timing motor 38. When the motor starts to run, the run switch 62 is closed which will keep the motor 38 energized during an entire measuring cycle. The cams 35, 36 and 37 inject reagent from the syringes into the reagent ports 21A, 21B or 21C in the analytical column.

At this time in the analysis cycle, the low spot on the cam 57 actuates the measurement switch 58. This applies the output of the measuring photocell 71 to the sample and hold circuitry. Note that this occurs at a time in the measuring cycle just prior to the time new reacted sample is added to the measuring cell 24. This allows the sample in the measuring cell to become completely reacted before a measurement is made.

Next, the nose 60 on cam 57 actuates a vertical lever 81 which lifts the silicon rubber plug in valve 23. This dumps a new volume of mixed sample and reagent from the float chamber into the measuring cell 24. Finally, the cam 57 rotates to a position at which the run switch 62 is open. This completes the cycle. A new cycle will not start until another precise volume of sample is dispensed from the metering chamber into the float chamber.

While a particular embodiment of the invention has been shown and described, various modifications will be apparent. The appended claims are, therefore, intended to cover any such modifications.

What is claimed is:

1. A colorimetric analyzer for automatically and continuously measuring the transmission of light through a sample which has been mixed with reagents comprising:
    a metering chamber for repeatedly metering precise volumes of said sample;
    sampling means coupled to said metering chamber for supplying a volume of said sample thereto;
    reagent dispensing means having an inlet adapted to receive a volume of a reagent and having an outlet coupled to an area within said analyzer in which a volume of said sample may be confined;
    a measuring cell coupled to said metering chamber for receiving measured volumes of said sample;
    a source of light positioned to direct light through a volume of sample disposed in said measuring cell;
    a photocell positioned for receiving light from said source which has traversed the sample disposed in said measuring cell;
    means coupling said metering chamber and said measuring cell for transferring said sample to said measuring cell so that the transmission of light from said source through the reacted mixture in said cell is measured by said photocell;
    indicator means;
    sample and hold circuit means coupling said photocell and said indicator means for applying the output of said photocell to said indicator means; and
    timing means actuating said sample and hold circuit means during time intervals when the reaction of said sample and reagents has been completed.

2. The colorimetric anaylzer recited in claim 1 wherein said source of light and said photocell are positioned in said measuring cell, said colorimetric analyzer further comprising:
    means for adjusting the relative position between said source of light and said photocell to accommodate analyses of samples having different light transmissions with full scale range of said indicator means.

3. The colorimetric analyzer recited in claim 1 wherein said reagent dispensing means includes a spool valve having an axial inlet and a radial discharge port, an elastomer sleeve around the circumference of said spool, whereby pressure applied to the inlet of said spool forces said reagent past said elastomer sleeve whereas reverse pressure seals the sleeve tightly on the radial port.

4. The colorimetric analyzer recited in claim 1 wherein said means for transferring said sample includes a float chamber between said metering chamber and said measuring cell, the precise volumes of said sample being transferred from said metering chamber to said float chamber said float chamber having a float actuated switch therein, and a timer started by said float actuated switch, said timer being connected to actuate said means for applying the output of said photocell to said indicator.

5. The colorimetric analyzer recited in claim 4 wherein reagent dispensing means are connected to at least two of said metering chamber, said float chamber and said measuring cell so that time-consuming chemical reactions progress simultaneously.

6. A colorimetric analyzer for automatically and continuously measuring the transmission of light through a sample which has been mixed with reagents comprising:

a metering chamber for repeatedly metering precise volumes of said sample;

sampling means coupled to said metering chamber for supplying a volume of said sample thereto;

a siphon tube having an entry end and a dispensing end, said siphon tube being positioned in said metering chamber so that upon accumulation of a quantity of fluid in said metering chamber a siphon action is started which delivers a precise amount of fluid through the dispensing end of said siphon;

reagent dispensing means having an inlet adapted to receive a volume of a reagent and having an outlet coupled to an area within said analyzer in which a volume of said sample may be confined;

a measuring cell coupled to said metering chamber for receiving measured volumes of fluid delivered by said siphon tube;

a source of light positioned to direct light through a volume of fluid disposed in said measuring cell;

a photocell positioned for receiving light from said source which has traversed the sample disposed in said measuring cell;

means coupling said metering chamber and said measuring cell for transferring said sample to said measuring cell so that the transmission of light from said source through the reacted mixture in said cell is measured by said photocell;

indicator means; and means for applying the output of said photocell to said indicator means during time intervals when the reaction of said reagents into said sample has been completed.

7. The colorimetric analyzer recited in claim 6 further comprising a vent tube positioned in said metering chamber with its lower end at the approximate level of the entry end of said siphon tube so that when sample closes the end of said vent tube, the next incremental amount of sample which enters said metering chamber starts a siphoning action which delivers a precise volume of fluid.

8. The colorimetric analyzer recited in claim 6 wherein the entry end of said siphon tube is larger in diameter than the remainder of said tube so that the surface tension of said sample is spread over a larger area whereby the meniscus in said entry end breaks at a repeatable point.

9. The colorimetric analyzer recited in claim 6 wherein the dispensing end of said siphon tube is biased to prevent drops of said sample from hanging to the end of said siphon thereby blocking the end of said siphon.

10. A colorimetric analyzer for automatically and continuously measuring the transmission of light through a sample which has been mixed with reagents comprising:

a metering chamber for repeatedly metering precise volumes of said sample;

sampling means coupled to said metering chamber for supplying a volume of said sample thereto;

reagent dispensing means having an inlet adapted to receive a volume of a reagent and having an outlet coupled to an area within said analyzer in which a volume of said sample may be confined;

a measuring cell coupled to said metering chamber for receiving measured volumes of said sample;

a source of light positioned to direct light through a volume of sample disposed in said measuring cell;

a photocell positioned for receiving light from said source which has traversed the sample disposed in said measuring cell;

means coupling said metering chamber and said measuring cell for transferring said sample to said measuring cell so that the transmission of light from said source through the reacted mixture in said cell is measured by said photocell;

indicator means;

timer means responsive to the presence of a precise volume of sample measured by said metering chamber;

and means actuated by said timer means for applying the output of said photocell to said indicator means during time intervals when the reaction of the reagents into said sample has been completed.

11. The colorimetric analyzer recited in claim 10 wherein said means for applying the output of said photocell includes a sample and hold circuit and a measuring switch, said measuring switch being connectd between said photocell and said sample and hold circuit, said measuring switch being actuated by said timer.

12. The colorimetric analyzer recited in claim 10 wherein said means for transferring said sample from said metering chamber to said measuring cell includes a valve actuated by said timer.

13. The colorimetric analyzer recited in claim 10 wherein said reagent dispensing means comprises syringe-like elements each including a plunger element, cams operated by said timer, said cams being positioned to actuate the plunger elements of said syringes to deliver volumes of reagent to said sample at desired times in each measuring cycle.

14. A colorimetric analyzer for automatically and continuously measuring the transmission of light through a sample which has been mixed with reagents comprising:

a metering chamber for repeatedly metering precise volumes of said sample;

sampling means coupled to said metering chamber for supplying a volume of said sample thereto;

a measuring cell coupled to said metering chamber for receiving measured volumes of said sample;

a source of light positioned to direct light through a volume of sample disposed in said measuring cell;

a photocell positioned for receiving light from said source which has traversed the sample disposed in said measuring cell;

reagent dispensing means having an inlet adapted to receive a volume of a reagent and having an outlet coupled to said metering chamber and said measuring cell so that time-consuming chemical reactions progress simultaneously in said metering chamber and said measuring cell;

means coupling said metering chamber and said measuring cell for transferring said sample to said measuring cell so that the transmission of light from said source through the reacted mixture in said cell is measured by said photocell;

indicator means; and means for applying the output of said photocell to said indicator means during time intervals when the reaction of said reagents into said sample has been completed.

15. In an analyzing instrument for receiving and automatically processing a liquid sample, said analytical instrument having a metering chamber for accumulating the liquid sample and including a bottom and a top portion, means for automatically transferring a precise, predetermined volume of accumulated sample from said metering chamber to a subsequent portion of said analyzing instrument comprising a siphon tube member arranged in an inverted U-shape, one leg of said U-shape being longer than the other and extending downwardly through said bottom of said metering chamber into said subsequent portion, said other leg terminating above said bottom and defining an entry end of said siphon tube member, and a vent tube extending into said chamber for venting said chamber while the level of the accumulated sample in the chamber is below the lowermost end of the vent tube.

16. The colorimetric analyzer recited in claim 15 wherein said vent tube is positioned in said metering chamber with its lower end at the approximate level of the entry end of said siphon tube so that when the sample closes the end of said vent tube, the next incremental amount of sample which enters said metering chamber starts a siphoning action which delivers a precise volume of fluid to said subsequent portion of said analyzing instrument.

17. The instrument recited in claim 15 wherein said one leg of said siphon tube is cut on a bias to prevent drops of said sample from hanging to the end of said siphon thereby blocking the end of said siphon.

* * * * *